United States Patent [19]

Merkl

[11] 4,072,699

[45] Feb. 7, 1978

[54] ALUMINUM ORGANOIODIDES

[76] Inventor: George G. Merkl, 46 Sunset Court, Haworth, N.J. 07641

[21] Appl. No.: 516,667

[22] Filed: Oct. 21, 1974

Related U.S. Application Data

[62] Division of Ser. No. 345,659, March 28, 1973, Pat. No. 3,856,841.

[51] Int. Cl.$^2$ .......................... C11C 1/00; C07F 5/06
[52] U.S. Cl. .................................... 260/408; 252/106; 252/107; 252/431 R; 252/431 C; 252/431 N; 260/414; 260/448 R; 260/448 A; 260/448 AD; 424/150
[58] Field of Search ............ 260/448 R, 448 AD, 414, 260/448 A, 346.1 M

[56] References Cited

U.S. PATENT DOCUMENTS

| | | | |
|---|---|---|---|
| 2,169,577 | 8/1939 | Bradley | 260/414 X |
| 2,417,071 | 3/1947 | Gebhart et al. | 260/414 |
| 2,422,798 | 6/1947 | Pines | 260/448 R |
| 2,473,434 | 6/1949 | Lindsey | 260/448 R X |
| 2,775,863 | 1/1957 | Traverse | 260/448 A |
| 2,867,643 | 1/1959 | Hamprecht et al. | 260/448 AD |
| 2,882,289 | 4/1959 | Appell | 260/448 R |
| 2,892,780 | 6/1959 | Rinse | 260/414 X |
| 3,214,450 | 10/1965 | Michaels | 260/414 |
| 3,214,451 | 10/1965 | Michaels | 260/414 |
| 3,287,384 | 11/1966 | Kearney | 260/414 |
| 3,399,221 | 8/1968 | Bertoni et al. | 260/448 A |
| 3,639,664 | 2/1972 | Schmank et al. | 260/448 AD |

OTHER PUBLICATIONS

Ushakov Chemical Abstracts, v24; p. 57 (1930).
Rabinovich, Chemical Abstracts, v41, p. 4732 (1947).
Udovtsova et al., Chemical Abstracts, v49, p. 7506 (1955).
Chivikova, Chemical Abstracts, v54, p.23311 (1960).
Liegler, Chem. Abst., v55, p. 3435 (1961).
Araka et al., Chem. Abst., v61, p. 14698$f$ (1964).
Skorobogat'ko et al., Chem. Abst., v71, 64921$z$ (1969).
Gude et al., Chem. Abst., v74, 54341$h$ (1971).
Mole et al., Organoaluminum Compounds, Elsevier Publ. Co., N.Y. pp. 10 & 11, (1972).

*Primary Examiner*—Helen M. S. Sneed

[57] ABSTRACT

An aluminum iodide is prepared by contacting a reactive aluminum with iodine and a liquid organic compound. The reactive aluminum is formed by permeating, in the presence of hydrogen ions, highly pure aluminum with a metal having an atomic volume close to that of hydrogen. Aluminum organoiodides are useful for detergents, catalysts, surgical scrubs, and other diverse applications.

10 Claims, 1 Drawing Figure

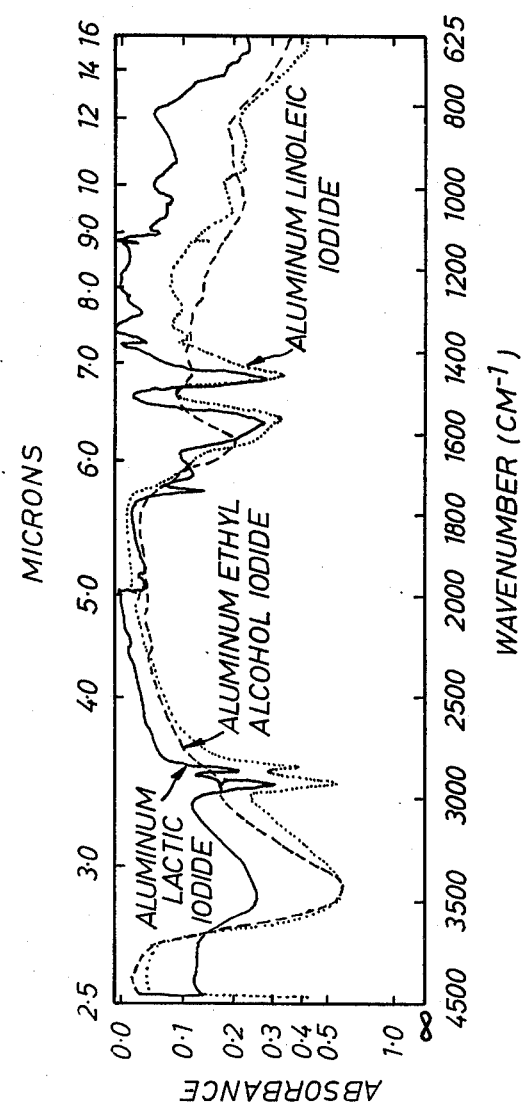

ALUMINUM ORGANOIODIDES

This is a division, of application Ser. No. 345,659, filed Mar. 28, 1973 now U.S. Pat. No. 3,856,841.

CROSS-REFERENCE TO RELATED APPLICATIONS

Reference is had to the following co-pending patent applications of applicant:

Catalytic Electrode Ser. No. 211,979, filed December 27, 1971, now abandoned;

Aluminum Salts Of Carboxylic Acids Ser. No. 255,757, filed May 1972, now abandoned;

Polymeric Salts Of Carboxylic Acids Ser. No. 255,758, filed May 22, 1972, now abandoned.

BACKGROUND OF THE INVENTION

The present invention relates to the formation of an aluminum organoiodide.

Generally, most commercial aluminum organoiodides appear to be focused about alkylaluminum iodides.

The most widely used types of aluminum organoiodides appear to be the alkylaluminum iodides. Basically, these compounds are an aluminum iodide with one or more of the iodide atoms replaced by alkyl groups. The standard method of production is by the reaction of metallic aluminum with an alkyliodide. Numerous modifications of operating conditions and catalysts to promote the reaction are known. For example, a mixture of aluminum chloride and alkylaluminum iodide can be added initially to start the reaction. An alternate catalyst procedure is the use of about 2.5% by weight of bromine or iodine and a small amount of a primary alkylchloride.

Alkylaluminum iodides are used as polymerization catalysts, especially in the presence of a small amount of a pure trialkyl aluminum. The range of polymerization applications is quite extensive.

Another application is for hydrogenating an unsaturated organic compound with a minimum of hydrocracking by heating to 250° to 400° C with hydrogen and an alkylaluminum iodide catalyst, having a ratio of aluminum to iodide between 1 to 2.25 and 1 to 1.5. Other applications include use in a Friedel-Crafts reaction to increase the yield of polysubstituted products and for the preparation of alkylsilanes and iodosilanes by the reaction of silica with an alkylaluminum iodide.

The products produced by the present methods go beyond the known products and have, in addition to the aforementioned application, application in detergents, for a cosmetic base, for inclusion in a soap as a germicide, and for use as a surgical scrub. Both gram positive and gram negative germs are killed by the present product.

SUMMARY OF THE INVENTION

Aluminum organoiodides are prepared in accordance with the present invention by contacting and reacting a. iodine;

b. an organic compound; and c. a reactive aluminum comprising high purity aluminum metal, e.g., aluminum metal having a purity of at least 99.99% by weight, permeated with from 0.1 to 5% by weight of a liquid metal selected from mercury, gallium, and indium/gallium alloys.

The organic compound is preferably an alcohol or an alcohol-carboxylic acid mixture. The organic compound can alternatively be a carboxylic acid alone, an aldehyde, a ketone, or a gaseous hydrocarbon such as methane or butane.

The aluminum organoiodides prepared have various uses, one of which is in the preparation of a germicidal scope.

BRIEF DESCRIPTION OF THE DRAWING

For a fuller understanding of the nature and objects of the invention, reference should be had to the following detailed description, taken in connection with the accompanying drawing, in which infrared spectracurves are given for aluminum linoleic iodide, aluminum lactic iodide, and aluminum ethyl alcohol iodide.

DESCRIPTION OF PREFERRED EMBODIMENTS

The present invention is focused on the utilization of the remarkable properties of a reactive aluminum prepared by the methods given in the aforementioned co-pending patent application, Catalytic Electrode.

The reactive aluminum in the present disclosure corresponds to the aluminum catalytic electrode described in the aforementioned co-pending patent application.

Generally, a reactive aluminum is prepared by contacting highly pure aluminum in the presence of a hydrogen ion source with a metal which can form a hydride. The hydrogen ion source can be an inorganic acid, such as hydrochloric acid or hydrobromic acid or the like, or an organic acid, such as citric acid or acetic acid, or the like. The reactive aluminum in an alkali solution such as water and sodium hydroxide will serve as an hydrogen ion source for the formation of another reactive aluminum.

The metal used for forming the reactive aluminum can be an element or an alloy. Preferably, the metal is gallium or indium, or an alloy of the two, or mercury. A desirable characteristic of the metal is that it is soft and pliable and preferably a liquid during the process in order to permit the rapid permeation or diffusion of the aluminum. The general rule is that a metal with an atomic volume near that of hydrogen is preferred.

It should be understood that the term "highly pure" herein means greater than 99.9% by weight and that purities in the order of 99.9% by weight or higher, are preferable.

One simple method of preparing a reactive aluminum is to use an aluminum piece, such as a rod, 99.9% pure by weight, having a length of about three inches and a diameter of about a half inch. The aluminum rod is placed on its side in a glass dish and sufficient 2N acid such as hydrochloric acid, is added to cover the aluminum rod. The aluminum rod is contacted with the metal, such as mercury or gallium, and the metal is given time to permeate the aluminum rod. Of course, the aluminum rod can be treated in a vertical position, if desired, and no special rod shape is necessary. Other shapes may be used.

The concentration of the acid can cover the broadest range to include almost neutral water. The choice of the hydrogen ion source, such as an acid, will depend upon the economics and the purity of the final product to be formed. For example, the use of hydroiodic acid as a hydrogen ion source for preparing the reactive aluminum avoids the introduction of impurities in the final product. This is in contrast to the use of hydrochloric acid, which might result in the presence of perhaps a trace of chlorine in the final products produced. Even if hydrochloric acid were used to prepare the reactive aluminum, a thorough washing of the reactive aluminum rod in water will minimize the presence of chlorine in the product to be produced.

It is preferable to prepare the aluminum rod for the reaction by at least partially stripping the aluminum oxide coating which invariably forms on the surface of aluminum, due to exposure to air and moisture. If the aluminum rod has been stripped, then hot water can serve as a hydrogen ion source, although the reaction time is quite long. Otherwise, it may be desirable to start out with a strong acid to strip off the oxide coating on the aluminum rod in order to initiate the permeation as quickly as possible. The aluminum rod may be stripped mechanically with sand paper or a file or the like.

The reaction to form the reactive aluminum proceeds as follows. At first, large bubbles are formed on the rod, and these bubbles rise to the surface of the acid. After a while, instead of large bubbles forming, tiny bubbles will appear to be emanating from many parts of the upper surface of the aluminum rod. The occurrence of the multitude of tiny bubbles indicates that the aluminum rod is being converted into a reactive aluminum as herein used.

Generally, the aluminum rod will take up or absorb from 0.1 to 5% by weight of the metal, say mercury, depending upon the length of time the permeation is permitted to continue. A range of 2 to 3% by weight of the mercury is preferable.

The permeation can be stopped on the basis of the increased weight of the aluminum rod due to the permeation of the metal or due to the production of a multitude of tiny bubbles for a period of 10 to 15 minutes, or due to the simple test of placing the aluminum rod in water and observing whether hydrolysis of the water takes place.

An aluminum rod, treated as described, displays surprisingly active properties not at all suggested by the prior art. The prior art has recognized that aluminum and an amalgam of aluminum exhibit active properties, but it is of considerable significance that the treatment of highly pure aluminum as described herein exhibits chemical properties that far exceed prior art contemplation.

Another method of preparing a reactive aluminum uses gallium instead of mercury. An aluminum rod, as described above, is placed in a glass dish and covered with hydrochloric acid and one end of the aluminum rod is contacted with the gallium, having a mass from 1 to 3% of the aluminum rod. The treatment takes from 10 to 15 minutes, depending upon how well the oxide coating on the aluminum rod has been removed at the point of contact of the gallium and the aluminum rod. A fairly clean part of the aluminum is indicated by the observance of large bubbles generated thereat.

It is desirable to dip a reactive aluminum formed with gallium into anhydrous alcohol immediately upon the completion of the process in order to prevent the formation of a brownish compound on the aluminum rod thereafter.

The amount of the metal in the aluminum rod can be varied. In general, if a higher percent of the metal by weight is desired, quick cooling of the reactive aluminum rod after formation will prevent the squeezing out of the metal. Water is convenient for this purpose. In cases where it is desirable to reduce the amount of the metal in the aluminum rod, the reactive aluminum can be heated to squeeze out the metal. For many applications, a mercury content of about 0.1% by weight is desirable.

From the above, it is clear herein, including the claims, what is meant by a "reactive aluminum."

The reactive aluminum exhibits an aligned matrix and, it is believed capable of converting, at least partially, to an hydride at one or more valences and produces $Al^{+++}$, $e^-$, $H^+$, $OH^-$, $HO_2^{--}$, and $O^{--}$, radicals depending upon the fluid contacting the reactive aluminum.

Certain impurities, such as copper and iron, inhibit the formation of a reactive aluminum and so should be avoided in the aluminum rod. Impurities which inhibit or promote the reaction are given in the aforementioned Catalytic Electrode application.

Generally, an aluminum alcohol iodide can be formed by combining an alcohol and iodine in the presence of a reactive aluminum. The choice of the alcohol can include a simple aliphatic alcohol, such as ethyl alcohol or an unsaturated alcohol, such as ethenol or a substituted aliphatic alcohol, such as ethanolamine or an aromatic alcohol such as benzyl alcohol or an alicyclic alcohol, such as cyclohexanol, or a heterocyclic alcohol such as furfuryl alcohol. The alcohol can also take the form a a glycol or other polyhydric alcohol, such as ethylene glycol, sorbitol or glycerol. Similarly, the term "alcohol" is used to embrace the related phenol. A carboxylic salt may be added to the alcohol and iodine to form a complex product, which includes the characteristic carboxylic organic radical.

Generally, in forming an aluminum alcohol iodide, the amount of iodine which becomes chemically bonded into the aluminum alcohol iodide will depend upon the mole ratio of the alcohol to iodine and the time that the reactive aluminum is permitted to react with the alcohol and iodine. As the reaction dynamics are not understood and believed to be extremely complex, the stoichiometry cannot be given with any precision. There are, however, empirical guidelines which have been determined.

If, for example, equal moles of iodine and ethyl alcohol are combined, the solution takes on a characteristic brown color. The introduction of a reactive aluminum results in a strongly exothermic reaction, which eventually results in a change in the color of the solution to a greenish-yellowish color. If an excess amount of iodine is used, the solution will retain a brown or dark brown color and at the completion of the reaction, a mixture of aluminum alcohol iodide with alcohol and dissolved iodine will result. If, on the other hand, the amount of iodine is equal to or just less than the quantity sufficient to fully react with the alcohol, completion of the reaction to form the aluminum alcohol iodide may be determined by analytically testing the solution for the presence of free iodine. Another method of monitoring the reaction to determine at least the approximate completion of the reaction is by measuring the mass of reactive aluminum used. When the mass of reactive aluminum has stabilized, it is an indication that the reactive aluminum is not continuing to form the aluminum alcohol iodide at an appreciable rate so that the reaction may be considered to be completed.

The amount of iodine which can be chemically combined with an alcohol will depend upon the chemical structure of the alcohol used. In addition, the addition of an organic compound, say a carboxylic acid, to the alcohol will further complicate the reaction dynamics.

Generally, if the alcohol used is miscible with water, then the aluminum alcohol iodide formed, will be both water and alcohol soluble and probably soluble in most hydrocarbon solvents.

As the reaction with the alcohol and iodine is highly exothermic, it is highly desirable to use a reflux system in order to avoid the excessive loss of alcohol due to evaporation.

The typical reaction permitted to go to full completion results in a polymer-like substance having a greenish-brown color. This product can be dried at 300° F and then pulverized to a powder. Known unsaturated organic iodides melt at less than 300° F and, in particular, iodoform explodes at less than 300° F.

In the case where the preferred quantity of iodine to alcohol is not readily known, it is convenient to use an amount of iodine less than what is believed to be the optimum, so that the formation of the desired product is assured without free iodine. This product will merely be in an alcohol solution and the alcohol can be distilled off to leave the desired product.

Some caution should be taken in carrying out the reaction to avoid excessive heat due to the chemical activity. For this purpose, the reaction vessel can be cooled. It is more convenient to add the iodine to the alcohol with the reactive aluminum in the alcohol over an extended period of time to prevent excessive heat buildup.

The reactive aluminum should be completely covered by the alcohol during the reaction in order to avoid the formation of additional products due to the reaction of the reactive aluminum and air.

The activity of the reactive aluminum used will depend, in part, on the metal which has been permeated into the aluminum and the percent by weight of the metal. It is desirable to use a reactive aluminum which shows relatively low activity in order to reduce the degree of the exothermic reaction. An example of a somewhat less active reactive aluminum is highly pure aluminum which has been permeated in the presence of hydrogen ions with mercury to about 3% by weight.

It is desirable to obtain the aluminum iodide product with a maximum purity and at worst, a trace of impurities such as mercury. Surprisingly, very little mercury appears in a product prepared with a mercury permeated reactive aluminum. This is because the mercury is not soluble in the solution and does not chemically combine with the compounds due to $H^+$.

It is known that as a reactive aluminum is reacting to form a product aluminum metal is taken up into the new product formed so that the percent by weight of mercury in the reactive aluminum increased gradually. A mercury permeated reactive aluminum which is permitted to react until all other aluminum has been consumed, will leave mercury at the bottom of the vessel. Therefore, the first rule for avoiding completely mercury contamination is to avoid consuming the mercury permeated reactive aluminum. The better rule is to use a relatively large quantity of reactive aluminum with respect to the alcohol so that the mass change in the total reactive aluminum is small, with a correspondingly small change in percent by weight of mercury in the reactive aluminum. Experience indicates that a reactive aluminum tends to retain the permeated metal readily to at least the order of 3 percent by weight.

Although the formation of the aluminum alcohol iodide is empirical, a great advantage is obtained by the fact that if the iodine to alcohol ratio is too high as evidenced by a persistent dark brwn color or verification of free iodine present or the presence of iodine crystals at the bottom of the vessel, one can simply add additional alcohol to further react the iodine to form the aluminum alcohol iodide.

Of course, additional compounds may be added to the alcohol and iodine to form novel products. For example, carboxylic acids may be added to the alcohol so that the product of the reaction is a complex containing aluminum, alcohol, iodine, and the characteristic group of the carboxylic acid. It is convenient to use alcohol soluble carboxylic acid for this purpose. The products formed with fatty acids are soluble in alcohol but not in water. These products lend themselves to use as surgical scrubs, germicides, fungus control, detergents and preservatives.

Omitting the alcohol so that only a carboxylic acid and iodine are used with the reactive aluminum leads to the formation of a product which can be generically called an aluminum carboxylic iodide.

It is preferable to use a carboxylic acid which is in a liquid form or which can be made into a liquid form conveniently. These products find application in the aforementioned areas, mentioned in connection with the aluminum alcohol iodide. The products made with fatty acids will be soluble in alcohol but not in water. The organic compound can also take the form of a ketone e.g., dimethyl ketone, ethylmethyl ketone or ethyl iso-propyl ketone. Similarly, the organic compound can be aldehyde, e.g., formaldehyde, acetaldehyde or butyraldehyde.

The organic compound can also take the form of a gaseous component, e.g., methane or butane.

The selection of the organic compounds used in the formation of the aluminum organoiodide should be guided by the ultimate application of the product. For example, it is known that myristic acid is used for the formation of base compounds for cosmetics. Then, an aluminum myristic iodide would be highly compatible with a cosmetic which is based on myristic acid. The aluminum myristic iodide would provide fungus control and germicidal protection needed for cosmetic bases.

It may be desirable to control fungus growth and bacteria growth in, say animal foods, by the use of an aluminum alcohol starch iodide. This can be prepared by merely adding starch to the alcohol and iodine and reacting with the reactive aluminum.

Another variation is to use glycerine with iodine and react with the reactive aluminum to form an aluminum glycerine iodide. It is known that glycerine is used in soaps to impart a high quality characteristic attractive to consumers. The use of aluminum glycerine iodide not only serves this function, but adds the feature of effectiveness in bacteria killing power.

In view of the high potency killing power of the aluminum organoiodides, incorporation into a soap or detergent is desirable. One general approach for accomplishing this is to first prepare an aluminum alcohol iodide. The aluminum alcohol iodide should be dried and pulverized to a powder. A cold addition of the powder to soap avoids the possible adverse reaction with sodium ions in the soap. Another way is to heat the soap to a liquid state and then add the aluminum alcohol iodide. Care should be taken to avoid a temperature which will break the bonds of the aluminum alcohol iodide. The aluminum organoiodides are highly desirable for use as a surgical scrub due to the germicidal powers.

A further appreciation of the aluminum organoiodides can be seen by reference to the figure which shows infrared spectra of aluminum linoleic iodide, aluminum lactic iodide, and aluminum ethyl alcohol iodide. The samples for each of the curves were prepared in a dry form and then mixed with potassium bromide to form a disc in accordance with the standard techniques. The scan speed of all of the samples was medium.

The analysis or interpretation of infrared spectra is a difficult and expanding art, but some comment can be made with respect to the figure, though no limitation is intended.

Broadly, it is known that the absorption in the region of about 3400cm$^{-1}$ can be attributed to the presence of hydroxyl groups. It is of interest that neither the curve for aluminum linoleic iodide or aluminum lactic iodide shows the characteristic absorption hands found for carboxylic acids or carboxylic esters. In the same way, it is of interest that the curve for aluminum ethyl alcohol iodide does not show the characteristic absorption bands for alcohol. The the infrared spectrum confirms that the product is not a mixture but is in fact a new compound.

EXAMPLES

Illustrative, non-limiting examples of the practice of the invention are set out below. Numerous other examples can readily be evolved in the light of the guiding principles and teachings contained herein. The examples are intended merely to illustrate the invention and not in any sense to limit the manner in which the invention can be practiced. The parts and percentages recited herein and all through this specification, unless specifically provided otherwise, refer by parts to weight and percentages by weight.

In the examples which follow, it is usually preferable to terminate the reaction by the removal of the reactive aluminum after the aluminum organoiodide has formed but before the reactive aluminum can react with the remaining organic compound to chemically change it. For example, it is known that the reactive aluminum will form a salt of a carboxylic acid so that after all of the iodine has been chemically combined with a carboxylic acid a salt of the carboxylic acid will form.

EXAMPLE 1

An aluminum ethyl alcohol is formed by combining one mole of iodine with two moles of ethyl alcohol ($CH_3CH_2OH$) in the presence of a reactive aluminum rod of about 100 grams. As the reaction is highly exothermic, the iodine should be added to the ethyl alcohol a little at a time, say about a ¼ of a mole every ten minutes. A system for reflux should be provided in order to avoid the loss of ethyl alcohol during the reaction. The reaction takes several hours and can be left for as long as 8 to 10 hours. Removal of the reactive aluminum terminates the reaction. A decided change in the color of the mixture will signal the transition from iodine dissolved in ethyl alcohol to the formation of the desired product. During the reaction, the solution may be cooled to reduce the evaporation of the ethyl alcohol. The product obtained may be dried to a powder by heating to about 150° F.

EXAMPLE 2

An aluminum ethenol iodide is formed by combining one mole of iodine and two moles of ethanol ($CH_2:CHOH$) in the presence of a reactive aluminum rod of about 200 grams. A reflux system may be used as well, as a means to cool the solution. The iodine should be added to the ethanol over an extended period of time in order to reduce the heat generated by the reaction.

EXAMPLE 3

An aluminum ethanolamine iodide is formed by combining one mole of iodine and two moles of ethanolamine ($NH_2CH_2CH_2OH$) in the presence of a reactive aluminum.

EXAMPLE 4

An aluminum benzyl alcohol iodide is formed by combining one mole of iodine with three moles of benzyl alcohol ($C_6H_5CH_2OH$) in the presence of a reactive aluminum. The precautions of EXAMPLE 1 are repeated by incorporation.

EXAMPLE 5

An aluminum cyclohexanol iodide is formed by combining one mole of iodine and four moles of cyclohexanol ($C_6H_{11}OH$) in the presence of a reactive aluminum.

EXAMPLE 6

An aluminum furfuryl alcohol iodide is formed by combining one mole of iodine and three moles of furfuryl alcohol ($C_4H_3OCH_2OH$) in the presence of a reactive aluminum.

EXAMPLE 7

An aluminum ethylene glycol iodide is formed by combining one mole of iodine and five moles of ethylene glycol in the presence of a reactive aluminum.

EXAMPLE 8

An aluminum glycerol iodide is formed by combining one mole of iodine and four moles of glycerol ($CH_2OH-CHOH-CH_2OH$) in the presence of a reactive aluminum.

EXAMPLES 9

An aluminum sorbitol iodide is formed by combining one mole of iodine as seven moles of sorbitol ($CH_2OH)(CHOH)_4(CH_2OH$) in the presence of a reactive aluminum.

EXAMPLE 10

An aluminum isopropyl alcohol iodide is formed by combining one mole of iodine and two moles of isopropyl alcohol ($CH_3CHCH_3OH$) in the presence of a reactive aluminum.

EXAMPLE 11

An aluminum butyl alcohol iodide is formed by combining one mole of iodine and six moles of butyl alcohol ($CH_3CH_2CH_2CH_2OH$) in the presence of a reactive aluminum.

EXAMPLE 12

An aluminum dimethyl ketone iodide is formed by combining one mole of iodine and four moles of dimethyl ketone (acetone) ($CH_3COCH_3$) in the presence of a reactive aluminum.

EXAMPLE 13

An aluminum ethyl methyl ketone iodide is formed by combining one mole of iodine and five moles of ethyl methyl ketone ($CH_3CH_2COCH_3$) in the presence of a reactive aluminum.

EXAMPLE 14

An aluminum ethyl iso-propyl ketone iodide is formed by combining one mole of iodine and eight moles of ethyl iso-propyl ketone ($CH_3CH_2COCHCH_3CH_3$) in the presence of a reactive aluminum.

EXAMPLE 15

An aluminum formaldehyde iodide is formed by combining one mole of iodine and three moles of formaldehyde (HCHO) in the presence of a reactive aluminum.

EXAMPLE 16

An aluminum acetaldehyde iodide is formed by combining one mole of iodine and five moles of acetyldehyde ($CH_3$—CHO) in the presence of a reactive aluminum.

EXAMPLE 17

An aluminum butyraldehyde iodide is formed by combining one mole of iodine and five moles of butyraldehyde in the presence of a reactive aluminum.

EXAMPLE 18

An aluminum phenol iodide is formed by combining one mole of iodine and nine moles of phenol ($C_6H_5OH$) in the presence of a reactive aluminum.

EXAMPLE 19

An aluminum linoleic iodide is formed by combining one mole of iodine and one mole of linoleic acid in the presence of a reactive aluminum.

EXAMPLE 20

An aluminum lauric is formed by combining one mole of iodine and three moles of lauric acid ($C_{11}H_{23}COOH$) in the presence of a reactive aluminum.

EXAMPLE 21

An aluminum formic iodide is formed by combining one mole of iodine and four moles of formic acid (HCOOH) in the presence of a reactive aluminum.

EXAMPLE 22

An aluminum lactic iodide is formed by combining one mole of iodine and five moles of lactic acid ($CH_3CHOHCOOH$) in the presence of a reactive aluminum.

EXAMPLE 23

An aluminum acrylic iodide is formed by combining one mole of iodine and three moles of acrylic acid ($CH_2:CHCOOH$) in the presence of a reactive aluminum.

EXAMPLE 24

An aluminum myristic iodide is formed by combining one mole of iodine and three moles of myristic acid ($C_{13}H_{27}COOH$) in the presence of a reactive aluminum.

EXAMPLE 25

Any of the examples, 1 to 17, can be repeated with the addition of one tenth of a mole of carboxylic acid soluble in the solution in the respective examples.

EXAMPLE 26

An aluminum glycerol iodide is formed by combining one mole of iodine and ten moles of glycerol in the presence of a reactive aluminum.

EXAMPLE 27

An aluminum butane iodide is formed by combining iodine vapor and butane ($C_4H_{10}$) in the presence of a reactive aluminum.

EXAMPLE 28

An aluminum methane iodide is formed by combining iodine vapor and methane ($CH_4$) in the presence of a reactive aluminum.

Having thus described the invention, what I claim as new and desire to be secured by Letters Patent, is as follows:

1. An aluminum alcohol iodide prepared by contacting and reacting:
   a. iodine;
   b. an alcohol selected from ethyl alcohol, ethenol, ethanolamine, benzyl alcohol, cyclohexanol, furfuryl alcohol, ethylene glycol, sorbitol, phenol, and glycerol; and
   c. a reactive aluminum comprising high purity aluminum metal permeated with from 0.1 to 5.0% by weight of a liquid metal selected from mercury, gallium and indium/gallium alloys.

2. Aluminum ethyl alcohol iodide having an infra-red spectrum curve substantially as illustrated in the Figure.

3. An aluminum carboxylic iodide prepared by contacting and reacting:
   a. iodine;
   b. a liquid carboxylic acid selected from myristic acid, linoleic acid, lauric acid, formic acid, lactic acid and acrylic acid; and
   c. a reactive aluminum comprising high purity aluminum metal permeated with from 0.1 to 5.0% by weight of a liquid metal selected from mercury, gallium and ind;ium/gallium alloys.

4. Aluminum lactic iodide having an infra-red spectrum curve substantially as illustrated in the Figure.

5. Aluminum linoleic iodide having an infra-red spectrum curve substantially as illustrated in the Figure.

6. An aluminum alcohol-carboxylic acid iodide complex prepared by contacting and reacting:
   a. iodine;
   b. an alcohol selected from ethyl alcohol, ethenol, ethanolamine, benzyl alcohol, cyclohexanol, furfuryl alcohol, ethylene glycol, sorbitol, phenol, and glycerol and a liquid carboxylic acid selected from myristic acid, linoleic acid, lauric acid, formic acid, lactic acid and acrylic acid; and
   c. a reactive aluminum comprising high purity aluminum metal permeated with from 0.1 to 5.0% by weight of a liquid metal selected from mercury, gallium and indium/gallium alloys.

7. An aluminum aldehyde iodide prepared by contacting and reacting:
   a. iodine;
   b. an aldehyde selected from formaldehyde and acetaldehyde; and c. a reactive aluminum comprising high purity aluminum metal permeated with from 0.1 to 5.0% by weight of a liquid metal selected from mercury, gallium and indium/gallium alloys.

8. An aluminum ketone iodide prepared by contacting and reacting:
   a. iodine;
   b. a di-lower alkyl ketone; and
   c. a reactive aluminum comprising high purity aluminum metal permeated with from 0.1 to 5.0% by weight of a liquid metal selected from mercury, gallium and indium/gallium alloys.

9. An aluminum glycerol iodide prepared by contacting and reacting:
   a. iodine;
   b. glycerol; and
   c. a reactive aluminum comprising high purity aluminum metal permeated with from 0.1 to 5.0% by weight of a liquid metal selected from mercury, gallium and indium/gallium alloys.

10. An aluminum hydrocarbon iodide prepared by contacting and reacting:
    a. iodine;
    b. methane or butane; and
    c. a reactive aluminum comprising high purity aluminum metal permeated with from 0.1 to 5.0% by weight of a liquid metal selected from mercury, gallium and indium/gallium alloys.

* * * * *